(12) United States Patent
Dewitt et al.

(10) Patent No.: US 11,045,648 B2
(45) Date of Patent: Jun. 29, 2021

(54) IRREVERSIBLE ELECTROPORATION THROUGH A COMBINATION OF SUBSTANCE INJECTION AND ELECTRICAL FIELD APPLICATION

(71) Applicant: BOSTON SCIENTIFIC SCIMED, INC., Maple Grove, MN (US)

(72) Inventors: Matthew Ryan Dewitt, Charlottesville, VA (US); Bruce R. Forsyth, Hanover, MN (US); Hong Cao, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 324 days.

(21) Appl. No.: 16/188,343

(22) Filed: Nov. 13, 2018

(65) Prior Publication Data

US 2019/0143106 A1 May 16, 2019

Related U.S. Application Data

(60) Provisional application No. 62/585,849, filed on Nov. 14, 2017.

(51) Int. Cl.
*A61N 1/32* (2006.01)
*A61N 1/04* (2006.01)
*A61B 18/14* (2006.01)
*A61B 18/00* (2006.01)

(52) U.S. Cl.
CPC .......... *A61N 1/327* (2013.01); *A61B 18/1477* (2013.01); *A61B 18/1492* (2013.01); *A61N 1/0416* (2013.01); *A61B 2018/00577* (2013.01); *A61B 2018/00613* (2013.01); *A61B 2018/00702* (2013.01); *A61B 2018/00875* (2013.01);
(Continued)

(58) Field of Classification Search
CPC .. A61N 1/327; A61N 1/0416; A61B 18/1492; A61B 18/1477; A61B 2018/1472; A61B 2018/00875; A61B 2018/00702; A61B 2018/1425; A61B 2018/00577; A61B 2018/00613
See application file for complete search history.

(56) References Cited

U.S. PATENT DOCUMENTS

| 5,019,034 A | 5/1991 | Weaver et al. |
| 5,370,675 A | 12/1994 | Edwards et al. |
| 5,718,246 A | 2/1998 | Vona |

(Continued)

OTHER PUBLICATIONS

StarBurst XL RFA Electrodes, Angiodynamics Inc. 2013. 2 pages.
(Continued)

*Primary Examiner* — Amber R Stiles
(74) *Attorney, Agent, or Firm* — Seager, Tufte & Wickhem LLP

(57) ABSTRACT

Biological cell destruction is achieved through a combination of injection of a substance and application of an electrical field. The substance, such as a cationic polymer, is selected for its electrical characteristics which can add to the transmembrane electric field of a cell when the electrical field is applied. In some examples, electrical field application is performed to encourage spatial concentration of the injected substance favorable to increased transmembrane field strength. The biological cell or cells are destroyed primarily through irreversible electroporation.

20 Claims, 16 Drawing Sheets

(52) U.S. Cl.
CPC ............... *A61B 2018/1425* (2013.01); *A61B 2018/1472* (2013.01)

(56) References Cited

U.S. PATENT DOCUMENTS

| | | | |
|---|---|---|---|
| 5,855,576 A | 1/1999 | Leveen et al. | |
| 5,863,290 A | 1/1999 | Gough et al. | |
| 6,010,613 A | 1/2000 | Walters et al. | |
| 6,041,252 A | 3/2000 | Walker et al. | |
| 6,043,066 A | 3/2000 | Mangano et al. | |
| 6,278,895 B1 | 8/2001 | Bernard | |
| 6,326,177 B1 | 12/2001 | Schoenbach et al. | |
| 6,387,671 B1 | 5/2002 | Rubinsky et al. | |
| 6,428,534 B1 | 8/2002 | Joye et al. | |
| 6,638,277 B2 | 10/2003 | Schaefer et al. | |
| 6,714,816 B1 * | 3/2004 | Heller ................... | A61N 1/325 604/20 |
| 6,912,471 B2 | 6/2005 | Heigl et al. | |
| 6,994,706 B2 | 2/2006 | Chornenky et al. | |
| 7,245,963 B2 | 7/2007 | Draghia-Akli et al. | |
| 7,306,595 B2 | 12/2007 | Ostrovsky et al. | |
| 7,306,940 B2 | 12/2007 | Miklavcic et al. | |
| 7,416,549 B2 | 8/2008 | Young et al. | |
| 7,456,012 B2 | 11/2008 | Ryttsen et al. | |
| 7,794,458 B2 | 9/2010 | McIntyre et al. | |
| 7,799,022 B2 | 9/2010 | Fernald et al. | |
| 7,850,681 B2 | 12/2010 | LaFontaine | |
| 8,014,854 B2 | 9/2011 | Schroeppel et al. | |
| 8,048,067 B2 | 11/2011 | Davalos et al. | |
| 8,114,070 B2 | 2/2012 | Rubinsky et al. | |
| 8,152,801 B2 | 4/2012 | Goldberg et al. | |
| 8,211,104 B2 | 7/2012 | McCullagh et al. | |
| 8,251,986 B2 | 8/2012 | Chornenky et al. | |
| 8,282,631 B2 | 10/2012 | Davalos et al. | |
| 8,465,484 B2 | 6/2013 | Davalos et al. | |
| 8,540,710 B2 | 9/2013 | Johnson et al. | |
| 8,603,087 B2 | 12/2013 | Rubinsky et al. | |
| 8,647,338 B2 | 2/2014 | Chornenky et al. | |
| 8,801,709 B2 | 8/2014 | Prakash et al. | |
| 8,915,911 B2 | 12/2014 | Azure | |
| 8,920,416 B2 | 12/2014 | Pham et al. | |
| 8,926,606 B2 | 1/2015 | Davalos et al. | |
| 9,005,189 B2 | 4/2015 | Davalos et al. | |
| 2001/0044596 A1 | 11/2001 | Jaafar | |
| 2002/0107515 A1 | 8/2002 | Edwards et al. | |
| 2002/0115991 A1 | 8/2002 | Edwards | |
| 2003/0009110 A1 | 1/2003 | Tu et al. | |
| 2004/0186468 A1 | 9/2004 | Edwards | |
| 2005/0267467 A1 | 12/2005 | Paul et al. | |
| 2006/0142801 A1 | 6/2006 | Demarais et al. | |
| 2006/0293730 A1 | 12/2006 | Rubinsky et al. | |
| 2007/0025919 A1 | 2/2007 | Deem et al. | |
| 2008/0275445 A1 | 11/2008 | Kelly et al. | |
| 2009/0247933 A1 | 10/2009 | Maor et al. | |
| 2009/0326638 A1 * | 12/2009 | Atanasoska ............ | A61L 31/16 623/1.15 |
| 2010/0023004 A1 | 1/2010 | Francischelli et al. | |
| 2010/0261994 A1 | 10/2010 | Davalos et al. | |
| 2011/0238057 A1 | 9/2011 | Moss et al. | |
| 2012/0053403 A1 | 3/2012 | Ducharme et al. | |
| 2012/0310230 A1 | 12/2012 | Willis | |
| 2012/0330299 A1 | 12/2012 | Webster et al. | |
| 2013/0184702 A1 | 7/2013 | Neal, II et al. | |
| 2014/0121663 A1 | 5/2014 | Pearson et al. | |
| 2014/0128859 A1 | 5/2014 | Lee | |
| 2014/0128936 A1 | 5/2014 | Laufer et al. | |
| 2016/0113709 A1 | 4/2016 | Maor | |
| 2016/0199661 A1 | 7/2016 | Willard et al. | |
| 2018/0250508 A1 * | 9/2018 | Howard ................ | A61B 5/0008 |

OTHER PUBLICATIONS

StarBurst Talon Infusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", PLOS One, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

\* cited by examiner

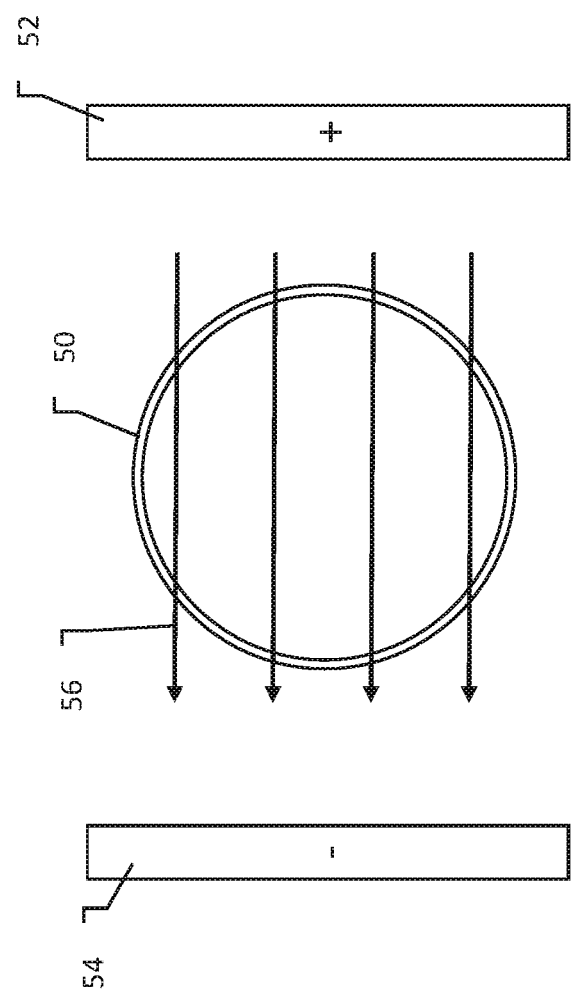

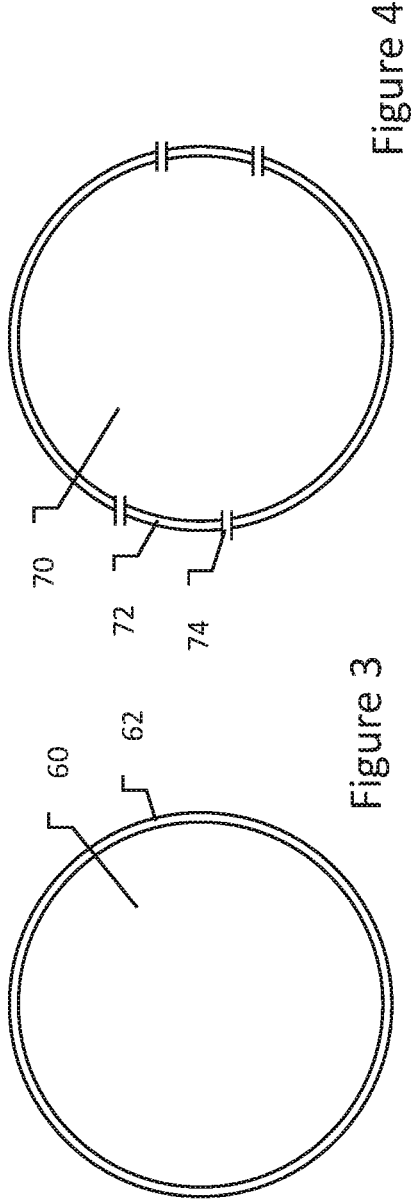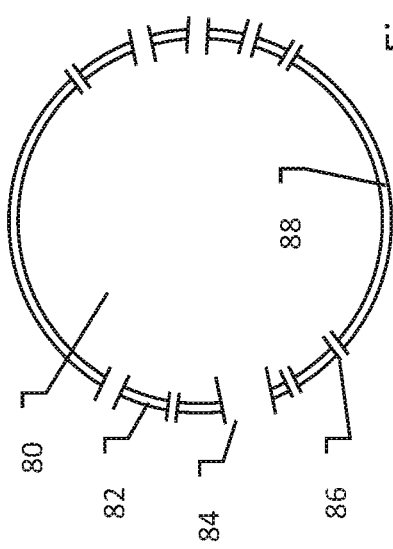

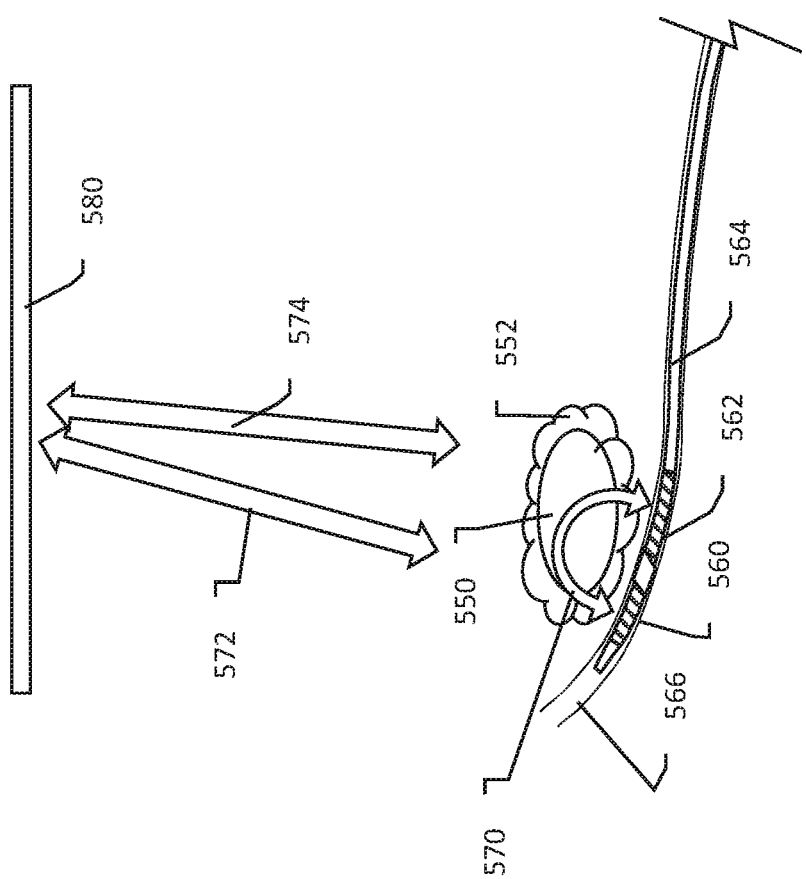

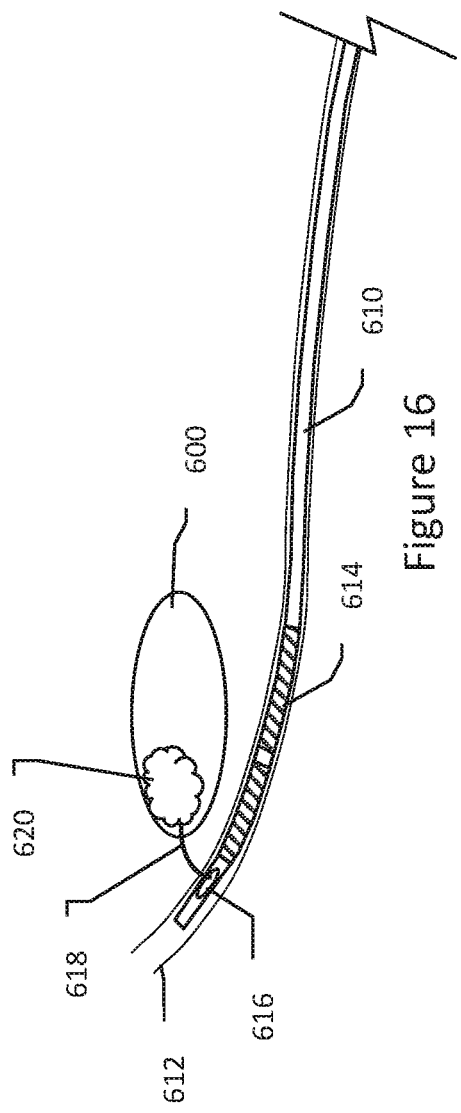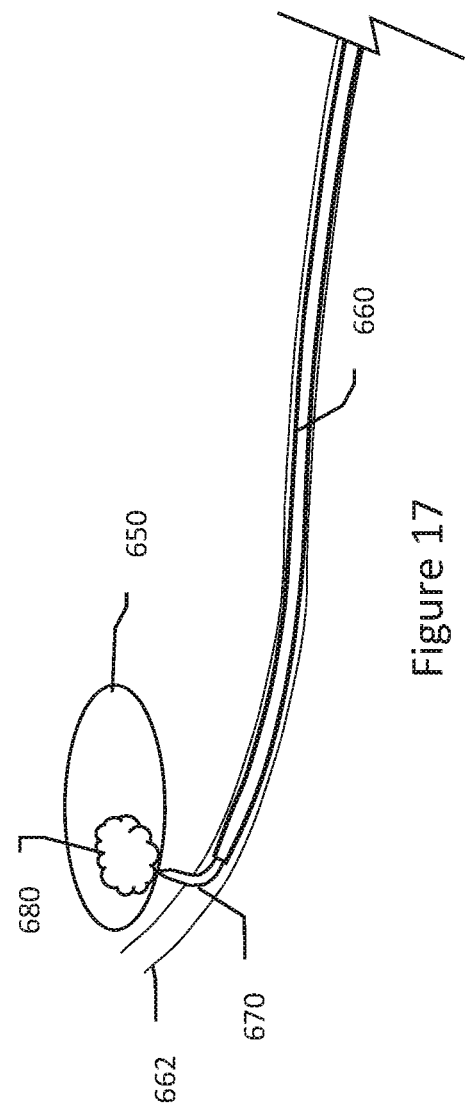

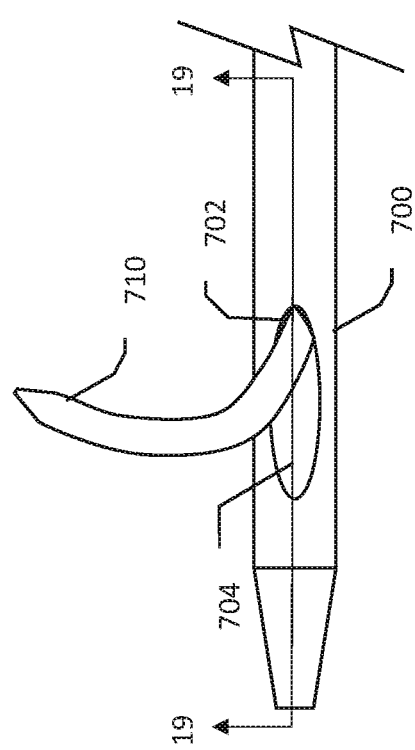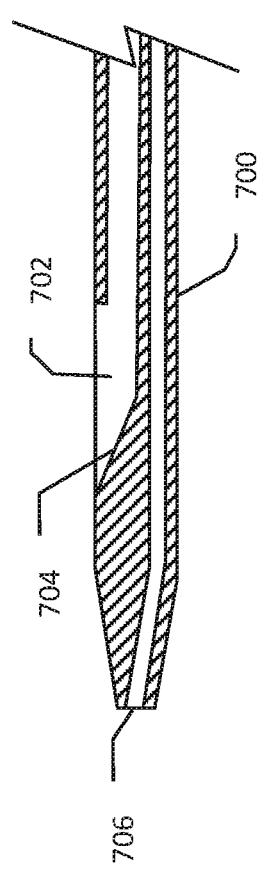
Figure 18
Figure 19

IRREVERSIBLE ELECTROPORATION THROUGH A COMBINATION OF SUBSTANCE INJECTION AND ELECTRICAL FIELD APPLICATION

RELATED APPLICATIONS

The present application claims the benefit of and priority to U.S. Provisional Patent Application Ser. No. 62/585,849, filed on Nov. 14, 2017, the disclosure of which is incorporated herein by reference.

BACKGROUND

A number of ablation modalities are used to treat biological tissue such as abnormal tissue including cancer. The various modalities known each have shortcomings. For example, thermal ablation (often using heat, but freezing is also possible) can be difficult to control in spatial extent, particularly with vascularized tissue, and can be non-specific, impairing the post-ablation healing process in the vicinity of tumor removal. Chemical ablation can have serious and sometimes systemic side effects. The various drawbacks of a number of such therapies are well known.

Electroporation is a phenomenon in which a biological cell responds to electrical fields by opening pores in the cellular membrane. When applied at relatively lower amplitude doses, electroporation has long been used to introduce material to biological cells that would not otherwise be able to pass through the cellular membrane. For example, genetic material or large molecules used in chemotherapy may be introduced to the interior of a cell. After removal of the electrical field, the induced pores close in "transient" or "reversible" electroporation.

At relatively higher amplitude electroporation doses, the pores that form in response to the applied electrical field can become so large that the cell membrane cannot recover. If the cell membrane does not recover, the cell will die due to this "irreversible electroporation." One difficulty with irreversible electroporation is that the amplitudes required are sufficiently high that other biological tissue can deleterious respond when used in-vivo, for example, through excitation of muscle tissue and cardiac cells. In addition, it is typically the goal to introduce electroporation (reversible or irreversible) without thermal effects or damage.

Various boundary conditions are pertinent to the field of electroporation. At low electric field strength, no pores form in the cellular membrane. Above an electroporation threshold, pores begin to reversibly form. Above an irreversible electroporation threshold, the pores that form irreversibly damage the cell, causing cell death. These thresholds vary with cell size and shape, overall tissue structure, and intercellular fluid characteristics. The thresholds themselves can be defined by local electric field strength and duration, for example where a higher amplitude voltage is needed at shorter durations, and lower amplitude voltage is needed at longer durations.

New and different approaches to biological tissue destruction are desired. In particular, new approaches to using irreversible electroporation for tissue ablation are desired.

OVERVIEW

The present inventors have recognized, among other things, that a problem to be solved is that of providing targeted ablation in a manner that removes or reduces the impact of various deleterious characteristics of prior methods. One element of such a solution may include decreasing the effective threshold for irreversible and reversible electroporation, allowing a reduced electric field to achieve desirable results. In an example, the present inventors have identified a combination of substance injection with electric field exposure, and more particularly using electric field characteristics designed and selected specifically to achieve synergy with the substance exposure. In an example, the substance to which the tissue is exposed comprises charged molecules, such as cationic polymers.

A first illustrative, non-limiting example takes the form of a method of treating targeted tissue of a patient comprising: injecting a cationic polymer in the targeted tissue; placing at least first and second electrodes in a position relative to the targeted tissue; delivering a series of biphasic waveforms after injection of the cationic polymer using the first electrode and second electrode as follows: in a first phase of a biphasic waveform, using the first electrode as the anode, and the second electrode as the cathode; and in a second phase of a biphasic waveform, using the first electrode as the cathode and the second electrode as the anode. The method may be further characterized as causing cellular death to the targeted tissue.

Additionally or alternatively to the first illustrative, non-limiting example, the step of delivering the series of electrical pulses may be performed after the cationic polymer is injected and before the cationic polymer has had time to accumulate on cells of the targeted tissue, such that the first pulse causes a concentration of the cationic polymer on a first side of at least one cell of the targeted tissue, the first side being nearer the first electrode than the second electrode, and the second pulse causes a concentration of the cationic polymer on the second side of the at least one cell, the second side of the at least one cell being nearer the second electrode than the first electrode.

Additionally or alternatively to the first illustrative, non-limiting example, the series of pulses may further include at least a third pulse and a fourth pulse; the third pulse may be delivered using the first electrode as the anode and the second electrode as the cathode, and an amplitude of the third pulse may be larger than an amplitude of the first pulse; and the fourth pulse may be delivered using the second electrode as the anode and the first electrode as the cathode, and an amplitude of the fourth pulse may be larger than an amplitude of the second pulse.

Additionally or alternatively to the first illustrative, non-limiting example, the first and second pulses may be delivered to cause desirable spatial distribution of the cationic polymer, and the third and fourth pulses may be delivered to cause irreversible electroporation of the at least one cell.

Additionally or alternatively to the first illustrative, non-limiting example, first pulse may have a pulse duration that is greater than a pulse duration of the third pulse, and the second pulse may have a pulse duration that is greater than a pulse duration of the fourth pulse.

Additionally or alternatively to the first illustrative, non-limiting example, the third pulse and the fourth pulse may each have pulse durations of less than 10 microseconds.

Additionally or alternatively, the third pulse and the fourth pulse may each have pulse durations of less than 1 microseconds.

Additionally or alternatively to the first illustrative, non-limiting example, the step of injecting a cationic polymer may be performed by inserting a syringe into the targeted tissue.

Additionally or alternatively to the first illustrative, non-limiting example, the step of injecting a cationic polymer may be performed by inserting a microcatheter into the vicinity of the targeted tissue.

Additionally or alternatively to the first illustrative, non-limiting example, at least one of the first and second electrodes may be disposed on a catheter that further comprises a lumen for delivering the cationic polymer, such that the step of injecting a cationic polymer may be performed by injecting the cationic polymer via the lumen.

Additionally or alternatively to the first illustrative, non-limiting example, an interpulse delay between the first pulse and the second pulse may be less than about 2 microseconds.

Additionally or alternatively to the first illustrative, non-limiting example, an interpulse delay between the first pulse and the second pulse may be less than about 100 nanoseconds.

A second illustrative, non-limiting example takes the form of a method of treating targeted tissue of a patient comprising injecting a cationic polymer in the targeted tissue; placing first and second electrodes in a position relative to the targeted tissue; delivering a series of electrical pulses after injection of the cationic polymer using the first electrode and second electrode as follows: in a first pulse, using the first electrode as the anode and the second electrode as the cathode and delivering the first pulse at a first amplitude for a first duration; and in a second pulse, using the first electrode as the anode and the second electrode as the cathode and delivering the second pulse at a second amplitude for a second duration; wherein the second amplitude is greater than the first amplitude and the second duration is shorter than the first duration. The method may be characterized as causing cellular death in the targeted tissue.

Additionally or alternatively to the second illustrative, non-limiting example, the method may be performed such that the first amplitude induces an electrical field in the targeted tissue of up to 500 volts per centimeter, and the second amplitude induces an electrical field in the targeted tissue of over 500 volts per centimeter.

Additionally or alternatively to the second illustrative, non-limiting example, the first duration may be greater than 10 microseconds, and the second duration may be less than 2 microseconds.

A third illustrative, non-limiting example takes the form of a method of treating targeted tissue of a patient comprising: injecting a cationic polymer in the targeted tissue; placing first and second electrodes in a position relative to the targeted tissue; delivering an electrical pulse to the targeted tissue after injection of the cationic polymer using the first electrode as anode and the second electrode as cathode by: in a first, initial portion of the electrical pulse, using a first amplitude for a first duration; and in a second, final portion of the electrical pulse, using a second amplitude for a second duration; wherein the second amplitude is greater than the first amplitude and the second duration is shorter than the first duration. Such a method may be characterized as causing cellular death in the targeted tissue.

Additionally or alternatively to the third illustrative, non-limiting example, the method may be performed such that the first amplitude induces an electrical field in the targeted tissue of up to 500 volts per centimeter, and the second amplitude induces an electrical field in the targeted tissue of over 500 volts per centimeter.

Additionally or alternatively to the third illustrative, non-limiting example, the first duration may be greater than 10 microseconds, and the second duration may be less than 2 microseconds.

A fourth illustrative, non-limiting example takes the form of a method comprising: (a) performing a method as in any of the first, second or third illustrative, non-limiting examples, (b) waiting at least 5 minutes; (c) measuring an impedance within the targeted tissue to determine whether a desired amount of irreversible electroporation has taken place and, if not, (d) again performing steps a-c.

Additionally or alternatively to an of the first to fourth illustrative, non-limiting examples, the methods may be performed such that the cationic polymer is delivered in an amount insufficient to substantially destroy the targeted tissue without application of the series of electrical pulses; and the series of electrical pulses are delivered at amplitudes and pulse durations that are insufficient to substantially destroy the targeted tissue without the cationic polymer.

A fifth illustrative, non-limiting example takes the form of a method of treating targeted tissue of a patient comprising: injecting a cationic polymer in the targeted tissue; placing at least first and second electrodes relative to the targeted tissue; and delivering a series of biphasic waveforms after injection of the cationic polymer using the first electrode and second electrode, such that at least the first electrode is used as an anode in a first phase of one of the biphasic waveforms, and as a cathode in a second phase of the one of the biphasic waveforms. The method may be further characterized as causing cellular death to the targeted tissue.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 show the application of an electrical field to a cell;

FIGS. 3-5 show various impacts of application of electrical field to a cell;

FIGS. 13-15 show therapy systems relative to an organ and target tissue in various configurations;

FIGS. 16-17 show applying a substance to or near a target tissue using different systems;

FIGS. 18-19 show a device useful for applying a substance in target tissue; and

DETAILED DESCRIPTION

Figure 1:
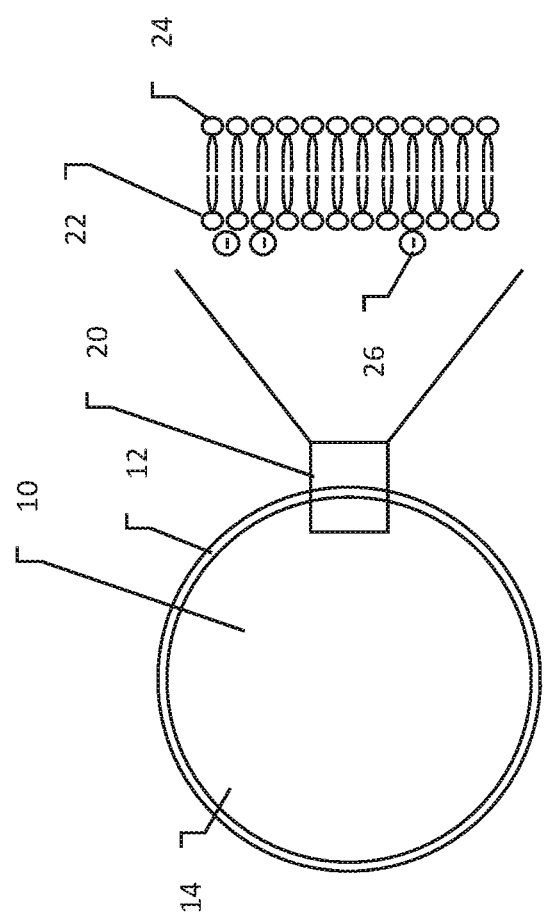
FIG. 1 shows a biological cell with focus on the cell membrane.

FIG. 1 shows a biological cell. The cell 10 contains a cytoplasm 14 within a cell membrane 12. The various well known contents of a cell are omitted for clarity. A detail view of the cell membrane 12 is shown at 20, where the phospholipid bilayer can be seen, having hydrophilic heads and hydrophobic tails. As is known to those skilled in basic cell biology, additional structures (not shown) are also present in the membrane 12 including integral membrane proteins and protein channels. The cell membrane 12 maintains a slightly negative charge within the cytoplasm, meaning there is an excess concentration of negative ions inside the cell membrane, as shown at 26, yielding a resting membrane potential in the range of −40 mV to −80 mV, typically around −57 mV in humans.

FIG. 2 show the application of an electrical field to a cell. FIG. 2 is highly schematic and suggests an in vitro approach in which a single cell 50 is placed between a positive plate or cathode 52 and a negative plate or anode 54. The concept however is far more widely applicable as shown below including for in vivo treatments.

The applied electrical field is shown illustratively at 56. It can be seen in FIG. 2 that the transmembrane potential for the cell 50 will be greatest on surfaces that face one or the other of the two plates 52, 54, and least at the portions of the cell wall that are parallel to the applied field. This causes electroporation in a spatially selective manner.

As described in U.S. Pat. No. 6,010,613, a transmembrane potential in the range of about one volt is needed to cause reversible electroporation. The required field may vary depending on characteristics of the cells to be treated. As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067.

The electric field for electroporation has typically been applied by delivering a series of individual pulses each having a duration in the range of tens to hundreds of microseconds. For example, U.S. Pat. No. 8,048,067 describes a series of eight 100 microsecond pulses delivered at 1 second intervals. More recent development has included the use of closely spaced, shorter duration pulses intended to have a cumulative effect on the cell membrane, as described in U.S. Pat. No. 8,926,606. Some discussion has taken place as well around the application of extra material, such as nanoparticles having surface adaptations directed to targeting and/or attaching to only abnormal cells (such as cancer cells), where the nanoparticles aid in reducing voltages needed to achieve cell destruction, as described in U.S. Pat. No. 8,465,484. For example, conductive particles attached to the cell membrane can reduce the driving threshold to the lipid bilayer by enhancing the local electric field around the nanoparticles themselves. Alternatively, nanoparticles may be used to increase local surface temperature on the cell membrane under the influence of external electrical or radiating fields. Even distribution of injected nanoparticles can be difficult to achieve within a target tissue volume. In contrast to these prior uses of nanoparticles, the present invention is more generally related to the use of cationic polymers or other charged particles that interact in synergy with an applied field on the cellular transmembrane potential.

FIGS. 3-5 show various impacts of application of electrical field to a cell. At electric field strengths below the threshold for reversible electroporation, as shown in FIG. 3, the cell membrane 62 of cell 60 remains intact and no pores occur. As shown in FIG. 4, at a higher electric field strength, above the threshold for reversible electroporation and below the threshold for irreversible electroporation, the membrane 72 of cell 70 develops pores 74. Depending on the characteristics of the applied field and pulse shapes, larger or smaller pores 74 may occur, and the pores developed may last for longer or shorter durations.

As shown in FIG. 5, at a still higher electric field strength, above the threshold for irreversible electroporation, the cell 80 now has a membrane 82 with a number of pores 84, 86. At this higher level, pores 84, 86 may become so large and/or numerous that the cell cannot recover. It may be noted as well that the pores are spatially concentrated on the left and right side of the cell 80 as depicted in FIG. 5, with few or no pores in the region 88 where the cell membrane is parallel to the applied field (assuming here that the field is applied as shown above in FIG. 2). This is because the transmembrane potential in region 88 remains low where the field is closer to parallel than orthogonal to the cell membrane.

Figure 6:
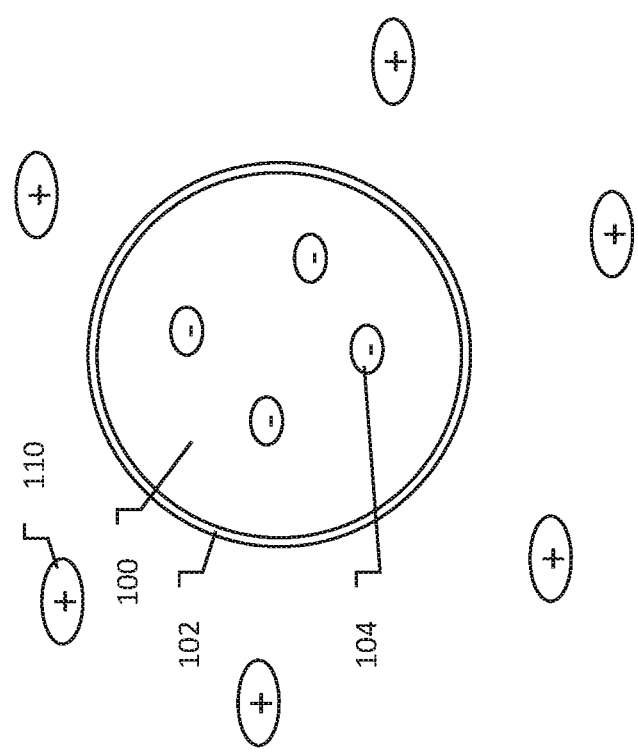
FIGS. 6-7 shows a biological cell in media having charged molecules therein.
Figure 7:
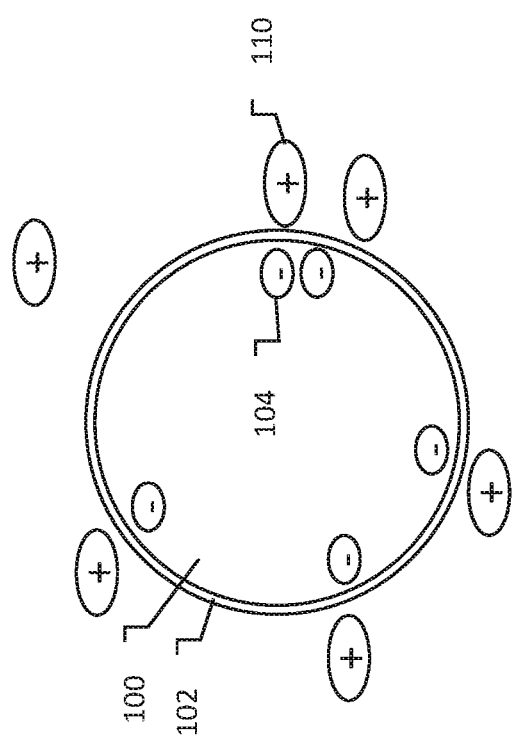

FIGS. 6-7 shows a biological cell in media having charged molecules therein. Starting in FIG. 6, the cell 100 with cell membrane 102 contains, as noted above, an excess of negatively charged ions 104 therein. A solution of positively charged molecules 110 can be introduced around the cell 100. Initially the charged particles are generally distributed equally as shown in FIG. 6. Within a short period of time, subject to factors such as concentration, temperature, viscocity, etc., electrostatic forces draw the positively charged molecules 110 to the negatively charged ions 104 in the cytoplasm on either side of the cell membrane as shown in FIG. 7.

Kennedy et al., in "Cationic Peptide Exposure Enhances Pulsed-Electric-Field-Mediated Membrane Disruption," PLoS One 9(3): e92528 (March 2014), list a number of substances including cationic peptides that may be used as the positively charged molecules 110. Kennedy et al. concluded the cationic peptides begin to affect cell membrane behavior within 300 to 400 seconds, at least at high concentrations, as the transmembrane fields generated by the positively charged molecules 110 and negatively charged ions 104 will exceed those needed for electroporation. This is suspected to be the driving force behind the toxicity of certain cationic peptides. However, such toxicity is difficult to use in vivo as there is a narrow window between no effect and too much toxicity. For this reason, a combination of cationic peptide exposure and electric fields was tested in Kennedy to witness cell membrane disruption.

Figure 8:
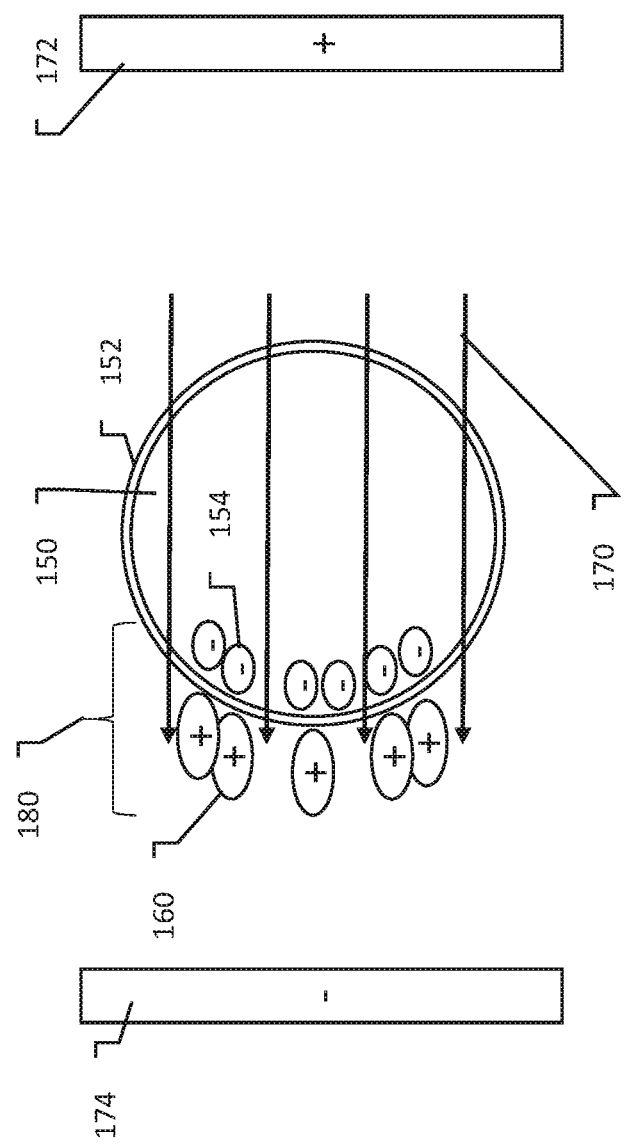
FIG. 8 show a cell and medium responding to an applied electrical field.

FIG. 8 shows in a summary form the cellular level result described by Kennedy et al. Cell 150, having cell membrane 152 and containing negatively charged ions 154 is in a medium having positively charged molecules 160. After injection of the substance containing the charged molecules 160 (which in Kennedy et al. comprised polyarginine cationic peptides in a salt solution), and before such molecules 160 spatially arrange themselves on the cell 150 (as shown in FIG. 7), an electric field is applied. In particular, Kennedy et al. ensured pulsed field delivery within 60 seconds of substance placement in the media near the cell—long enough to allow dispersion of the molecules 160 in the extracellular media, but not so long that electrostatic forces take hold. The positively charged ions were thus drawn to the anodic plate 174, being pushed in that direction by the applied field, creating an area of increased concentration 180 of the molecules 160 and ions 154 on the cell membrane. When combined with the applied, monophasic field, this concentration 180 was believed to make irreversible electroporation more likely at lower voltages than might otherwise be required. Kennedy et al. were able to show that the extent of electroporation across a cell population increased at a given electrical field level with the addition of higher concentrations of cationic peptides. Thus, for the in vitro experiment of Kennedy et al., 25 micrograms per milliliter concentration of the chosen material meant the difference between no cells exhibiting any electroporation and the majority of cells exhibiting delayed irreversible electroporation for the same applied field.

In Kennedy et al., the spatial concentration at 180 appears to have been a focus of the experiment. To achieve this, the electrical therapy must be delivered very quickly after injection of the charged molecules. However, in vivo, it is common to monitor progress by measuring impedance changes over time. Such measurements can introduce delay between therapy applications, making the spatial management suggested in Kennedy et al. challenging to use throughout a course of therapy. Thus a different approach is desirable.

Figure 9:
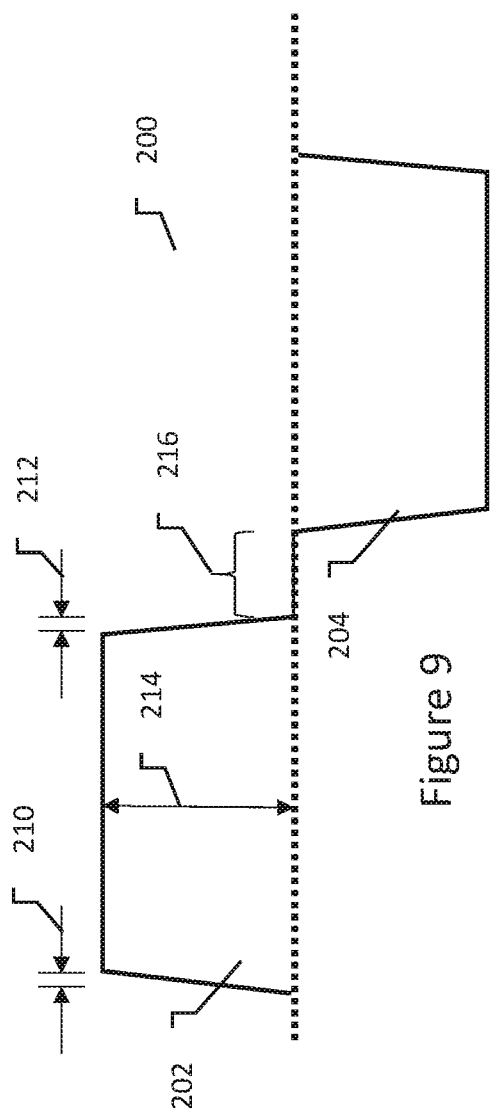
FIG. 9 shows an illustrative therapy waveform.

FIG. 9 shows an illustrative therapy waveform. A biphasic waveform is shown at 200, with a first, positive phase 202, and a second, negative phase 204. The waveform may be characterized at least in part by features such as rise time 210, fall time 212, amplitude 214, and interpulse delay 216. The rise and fall times 210, 212 determine how sharp the edges of therapy pulses are, for example, the rise time 210 is the time from waveform onset until the output reaches the desired amplitude 214. Different pulse generators may have different limitations in this regard. The interpulse delay determines how much time passes from the end of the positive phase 202 until the start of the negative phase 204. Features 210, 212, 214 and 216 may in some pulse generators allow user settings within defined limits; in some systems the rise and fall times 210, 212 may be preset. Like features may be defined for the negative phase 204.

Kennedy et al. teach a monophasic output, that is, something generally resembling just one phase 202, omitting the latter portion 204 of the signal. The present inventors have recognized an improvement on the approach in Kennedy et al. is to apply a biphasic waveform, while reducing the interpulse delay 216 as much as possible to achieve a significant reversal of the electric field, subjecting a greater area of the cell membrane to electrical fields that may enhance the likelihood of electroporation through the combined effects of the cationic polymer and externally applied electric field on the inducted transmembrane potential. Thus in one example, a method of cell ablation comprises injecting or otherwise applying a substance having charged molecules (such as a cationic polymer) and then applying a biphasic waveform to generate first and second electric fields that cause electroporation in cooperation or synergy with the applied substance over a greater area of the cellular membranes in the targeted region.

Figure 10:
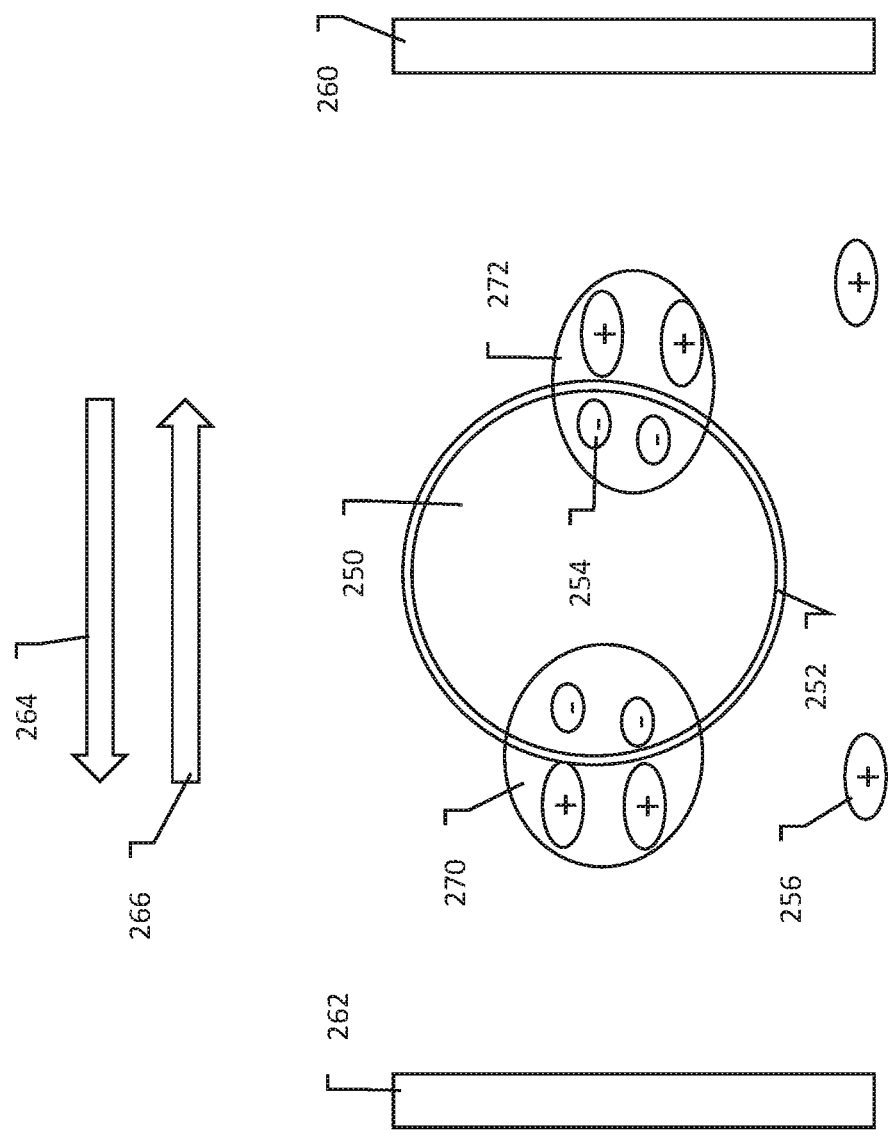
FIG. 10 shows an effect of using a biphasic waveform with charged molecules in the intercellular fluid.

FIG. 10 shows use of a biphasic waveform with charged polymers in the intercellular fluid. The cell 250 with membrane 252 has excess negative ions 254 therein, and is shown in an extracellular medium having excess positively charged particles 256. Electrodes 260, 262 are shown on opposing sides of the cell 250. On delivery of the first phase 264 of the biphasic waveform, at least some of the positive particles 256 are drawn toward one of the electrodes 262 that serves as the anode for the first phase. Thus some degree of accumulation will occur as shown at 270, with positively charged external particles electrostatically held more or less on the surface of the cell membrane with negatively charged ions in close proximity inside the cell membrane 252. On delivery of the second phase 266 of the waveform, other positive particles 256 are drawn toward the other of the electrodes 260, yielding another region of concentration of negative and positive particles on the cell membrane 252.

The resulting arrangement as shown in FIG. 10 has areas at 270, 272 with relatively higher concentrations of charged particles electrostatically attracted to one another across the cell membrane 252. With greater surface area affected, it is believed that the resulting likelihood of irreversible electroporation is enhanced for subsequent delivery of biphasic energy. A number of more particular waveforms are disclosed below that may be useful in this biphasic format.

In another example, a biphasic waveform is applied in an imbalanced manner, with a first phase having a lower amplitude than the second phase. In a further example, the higher amplitude second phase may also have a shorter duration than the lower amplitude first phase. In such an approach, the first phase can have lower amplitude as the field between ions in the cell and the charged molecules outside the cell is additive to the applied field. The second phase can have a higher voltage as it spatially targets the region of the cell where charged molecules have not accumulated in the first phase, thus a higher voltage to induce electroporation without the aid of the additive field from the molecules/ions. To avoid muscle stimulation and/or heating, the second phase can have a shorter duration.

In some examples, prepulsing at relatively lower voltages may be used to distribute the charged molecules in a spatial pattern, with subsequent pulses applied at higher voltages to then drive electroporation after the molecules are in desirable positions. Given that the injected charged molecules may take some period of time to distribute themselves onto the cell membranes, it seems desirable to provide relatively longer pulses to achieve such distribution. However, long pulses at high amplitudes can generate heat and/or recruit muscle, causing painful movements to the patient. Therefore in addition to changing the applied voltage level, the duration of prepulsing waveform may be longer than the duration of the electroporation-inducing waveform. The prepulsing may be performed using pulses in the range of tens or hundreds of microseconds to tens of milliseconds, with later, higher voltage pulses delivered at shorter durations.

Figure 11:
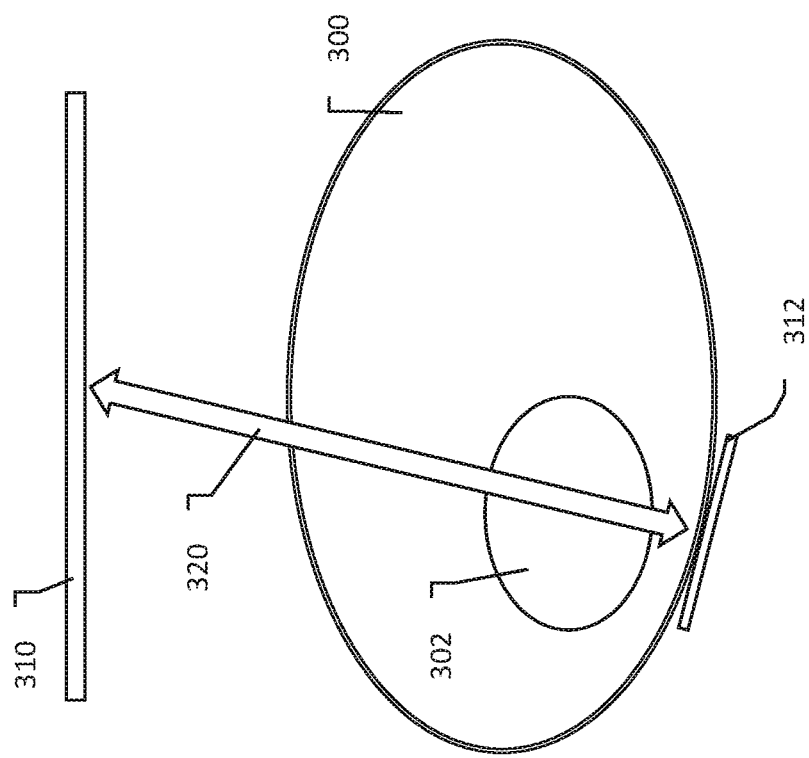
FIG. 11 shows a therapy system relative to an organ and target tissue.

FIG. 11 shows a therapy system relative to an organ and target tissue. The illustration focuses on the electrodes used for therapy delivery, and further examples below show a more complete system. In the example, a monopolar approach is taken with an organ 300 having target tissue 302 therein. For example, the organ 300 may be the liver, and the target tissue may be a hepatic cancer 302. A first electrode is shown at 310 and a second electrode at 312, with the organ 300 and target tissue 302 generally between electrodes 310, 312. In the example, electrode 310 may be a "return" electrode disposed on the surface of the patient's skin (possibly using a hydrogel or the like to enhance electric coupling to the skin) having a relatively large surface area. Electrode 312 may be disposed in, on, or adjacent to the organ 300 as by, for example, placement on a catheter extending into a blood vessel or other luminal structure near, on, or through the organ 300, or which is advanced by tunneling or cutting a tissue tunnel where none previously existed. This electrical therapy delivery is to be combined in various illustrative embodiments with delivery of a substance which, combined with the electrical therapy, provides a synergistic effect as described below.

A biphasic therapy signal is then applied, as indicated at 320. It should be noted that, as used herein, "biphasic therapy" is intended to be defined expansively to indicate therapy having multiple phases during which the electrical field direction is modified from one phase to the next. If more than two phases are included, this is to be considered biphasic as well, so long as the pulses are directionally distinct from one another. A system having two electrodes A, B, can deliver a biphasic signal, as used herein, by having electrode A serve as anode and then cathode, and electrode B serve as cathode and then anode during delivery of the therapy. A system having three electrodes A, B, C may deliver a biphasic signal by generating a series of pulses/fields in which any of A, B, or C switches from being an anode during one phase to being a cathode during another phase. A system having more than three electrodes may deliver a biphasic signal by generating a series of pulses/fields in which a first phase and a second phase are delivered using different spatial vectors or, if at least one electrode is used as an anode in one phase and as cathode during a different phase.

Figure 12:
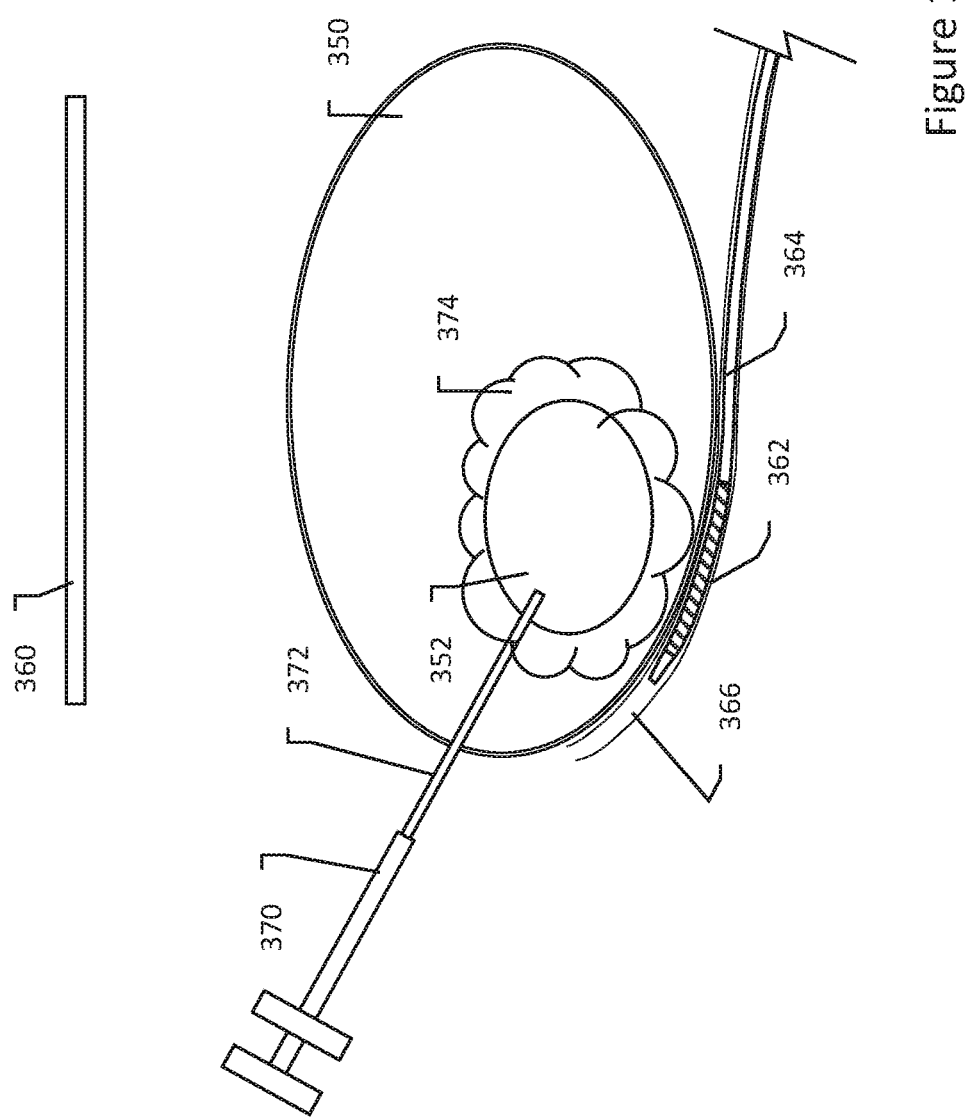
FIG. 12 shows one approach to apply a substance to or near a target tissue.

FIG. 12 shows one approach to apply a substance to or near a target tissue. An organ 350 is shown having a target tissue 352 therein. A syringe 370 having a needle/penetrating portion 372 can be used to inject a solution of a desired substance in a suitable solvent in and near the target tissue 352. For example, a cationic polymer may be dissolved, suspended or otherwise mixed with a biocompatible liquid. In a specific example, a salt or saline solution is used as the biocompatible liquid, and cationic polyarginine as the cationic polymer. As used herein, the term cationic polymer includes both polymers that carry or have a cationic charge, as well as peptides and/or peptide/polymer combinations that have a cationic charge. Concentrations may be in the range of, for example, 100 micrograms per milliliter up to about 500 micrograms per milliliter, or less or more. Several milliliters of such fluid may be provided, depending on the size of the target tissue 352. The injection may include moving the needle about, for example by entering to a first extent, injecting a quantity, advancing or moving the needle, and then injecting another quantity of the material. A sufficient amount of the injected material is desirably used to encompass the targeted tissue, as indicated at 374. In other examples, the injected material may only be injected in a portion of the target tissue 352. For example, multiple small injections may be made over time to accommodate a larger tissue target which may require multiple treatments.

In several examples described herein, a cationic polymer is injected, applied or provided for purposes of enhancing the effects of the electrical field to be applied. In other examples, a macromolecule having properties that are adapted to affect a cell membrane itself, rendering the cell membrane more susceptible to poration in the presence of an electrical field, or more likely to fail to recover from poration (rendering the poration irreversible and leading to cell death), may be applied instead of or in addition to a cationic polymer. Any substance having the tendency to activate, or inactivate, a cell membrane characteristic that renders the cell membrane more susceptible to poration or less likely to recover from poration, may be used.

One challenge with the injection mode shown in FIG. 12 is that of track seeding, in which living cancerous cells can stick to the needle 372 and drop off along the track formed by the needle. As the needle is withdrawn, the cells that track along the track will be moved away from the region where electrical energy is to be later applied, meaning that such cells are likely to survive the electroporation therapy. Other modes of delivery are also shown below that may avoid such a phenomenon.

FIG. 12 shows some additional details relating to the electrical therapy delivery system. In the example, electrode 360 is again shown as a distant electrode and may be, for example, on the patient's skin. Electrode 362 is shown as a coil electrode mounted on a catheter 364 that has been advanced through a lumen 366. Lumen 366 may be, for example, a blood vessel or another body lumen such as a biliary or lymph duct. The catheter 364 includes electrical conductors through the body thereof to a proximal connector that can in turn couple to an external pulse generating system.

Figure 13:
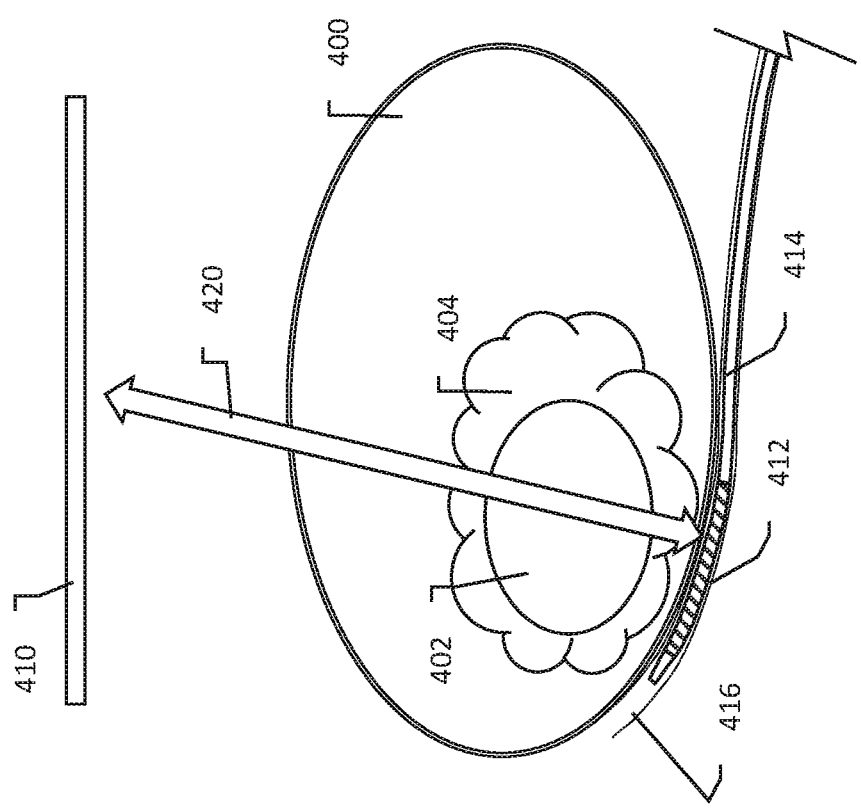
Figure 14:
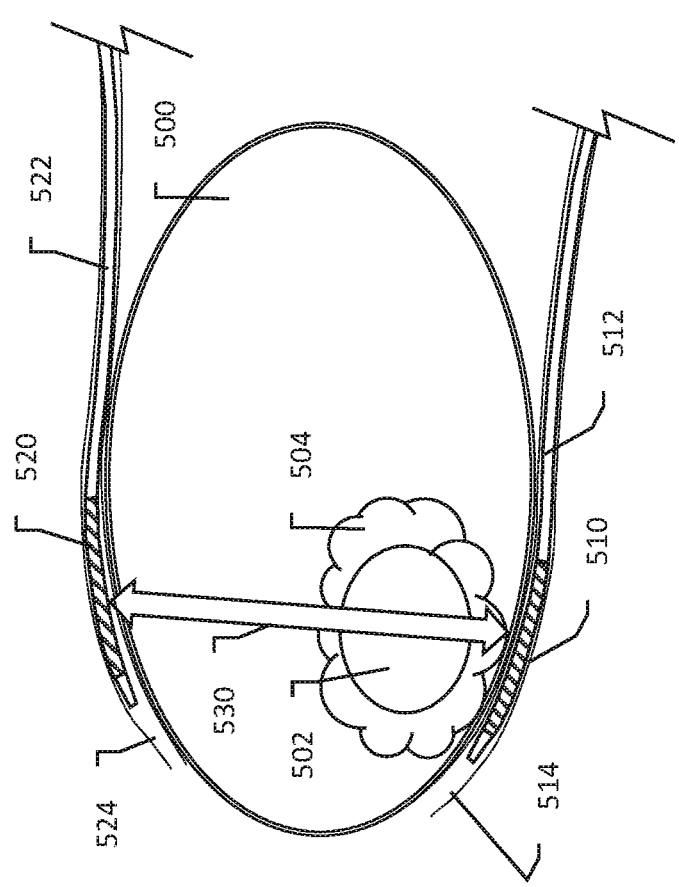

FIGS. 13-15 show therapy systems relative to an organ and target tissue in various configurations. Turning first to FIG. 13, a configuration similar to that of FIG. 12 is shown with an organ 400 having a target tissue 402 therein. A substance, such as a biocompatible liquid containing a cationic polymer, has been injected in the region 404 of the target tissue 402. A first electrode 410 is disposed at a first location, with the first electrode 410 being shown as a surface electrode on the patient's skin; other locations may be used. A second electrode 412 is shown on a catheter 414 that has been placed via a body lumen 416 at a location near the organ 400 and/or target tissue 402.

Biphasic electrical therapy is then delivered with characteristics selected to achieve irreversible electroporation when used in conjunction with the injected substance. Some example therapies may be understood with reference to FIG. 9 and FIGS. 20-23. Some illustrative examples are as follows:

A simple biphasic therapy as shown in FIG. 9 may be delivered with an interpulse delay 216 that is less than about 2 microseconds; preferably, less than about 100 nanoseconds; and still more preferably less than about 10 nanoseconds. The sudden switch in polarity is likely to prevent release of localized concentrations of the injected substance on the cell membrane, preservation of which increases the likelihood that induced pores become irreversible. The injected material may reduce the needed amplitude for the electrical field to cause irreversible electroporation in a given tissue volume. In an example, the applied pulses have durations in the range of about 1 to about 1000 microseconds, preferably about 5 to about 100 microseconds, and more preferably about 10 to about 50 microseconds. The biphasic delivery may be repeated a number of times, for example, at 1 second intervals for a total of 8 deliveries of the biphasic waveform. The amplitude may be selected to generate an electrical field in the range of about 500 to about 5000 V/cm, more preferably about 750 to about 2000 V/cm, and still more preferably about 900 to about 1500 V/cm, within the desired tissue volume. Other durations and waveforms may be used. For example, the simple biphasic therapy may be delivered in bursts of several cycles, such as by delivering 2 to 12 sets of 4 to 12 waveforms as shown in FIG. 9 at within-burst intervals of 10 to 1000 microseconds, with each set starting at 1 second intervals and with the waveforms comprising pulse durations in the range of 100 to 10,000 nanoseconds at amplitudes in the range of about 750 to about 2000 V/cm in the desired tissue volume.

Figure 20:
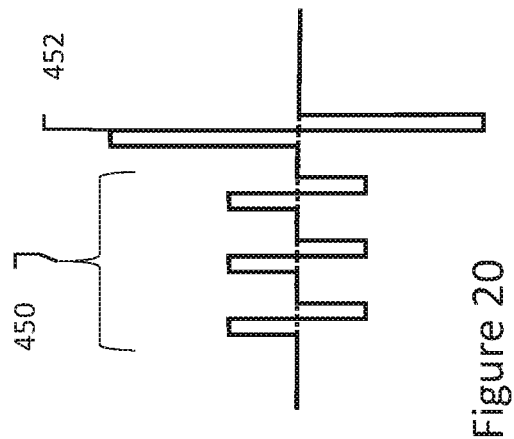

A more complex therapy waveform may be as shown in FIG. 20, in which one or more biphasic waveforms of lesser amplitude are delivered in a set 450 followed by a biphasic waveform at 452 at higher amplitude. The set of lesser amplitude waveforms 450 may be adapted to drive the positioning of the extracellular charged molecules on the cell membrane in preparation for a higher amplitude waveform 452 adapted to cause irreversible electroporation in conjunction with the electric fields generated across the cell membrane by the injected particles. If desired, the larger amplitude pulse 452 may be repeated standing alone or the combination of lower amplitude pulses 450 and the large amplitude pulse 452 may be repeated entirely. In an example, the lower amplitude pulses 450 are at a voltage that is below a threshold for irreversible electroporation, such as under about 650 V/cm in the desired tissue region, or may be below a threshold for reversible electroporation, such as in the range of under about 350 V/cm in the desired tissue region, with the larger amplitude pulse delivered at an amplitude above 650 V/cm, such as in the range of about 750-5000 V/cm in the desired tissue region. In an example, the larger amplitude pulse 452 has an amplitude that is at least twice that of the lesser amplitude pulses 450. Pulsewidth may be in the range of about 1 to about 1000 microseconds, preferably about 5 to about 100 microseconds, and more preferably about 10 to about 50 microseconds. Interpulse delay may again be relatively short, such as less than about 2 microseconds; preferably, less than about 100 nanoseconds; and still more preferably less than about 10 nanoseconds. The biphasic waveforms may be spaced from one another by an interval in the range of about 10 to about 1000 microseconds.

Figure 21:
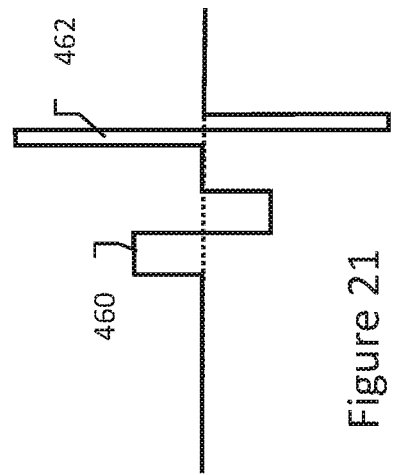
FIGS. 20-23 show illustrative therapeutic waveforms.

In another example, multiple parameters are varied between consecutive biphasic waveforms, as shown in FIG. 21. Here, a wider pulsewidth, lower amplitude biphasic waveform 460 precedes a shorter pulse width and higher amplitude biphasic waveform 462. In the example, waveform 460 is at a lower amplitude meaning that a longer duration is less likely to induce either muscle stimulus or thermal effects, while waveform 462 is at a shorter pulsewidth meaning that the higher voltage is less likely to induce muscle stimulus or thermal effects. If desired, waveform 462 may be repeated. Again, the first delivered waveform 460 is delivered to induce desirable spatial concentrations of the injected substance, and the second waveform 462 is delivered to induce irreversible electroporation when combined with the transmembrane electric field generated by the injected substance. The first waveform 460 may have, for example, a pulsewidth in the range of about 5 to about 1000 microseconds, preferably about 10 to about 100 microseconds, and more preferably about 20 to about 50 microseconds, while the second waveform has a pulsewidth of about 500 nanoseconds to about 500 microseconds, preferably about 1 to about 50 microseconds, and more preferably about 5 to about 20 microseconds, wherein the pulsewidth of the first waveform 460 exceeds that of the second waveform 462, preferably wherein the pulsewidth of the first waveform 460 is at least double that of the second waveform 462, and still more preferably wherein the pulsewidth of the first waveform 460 is at least quadruple that of the second waveform 462. The amplitude of the first waveform 460 may be less than an irreversible electroporation threshold, or in a further example, less than a reversible electroporation threshold. For example, the first waveform 460 may have an amplitude in the range of up to about 600 volts, or, in another example, up to about 350 volts. The amplitude of the second waveform 462 is larger than the amplitude of the first waveform 460, more preferably at least twice the amplitude of the first waveform 460. In another example, the amplitude of the second waveform 462 is in the range of above 650 V/cm, such as in the range of about 750-5000 V/cm.

Amplitude values herein are recited in terms of V/cm in order to account for variations in the location and types of tissue to be treated, as the electrodes used to treat a larger tumor may be several centimeters apart from one another, while in other examples such as tumors along a luminal surface, the electrodes may be a centimeter or less apart with a tumor that is but a few millimeters across.

Figure 22:
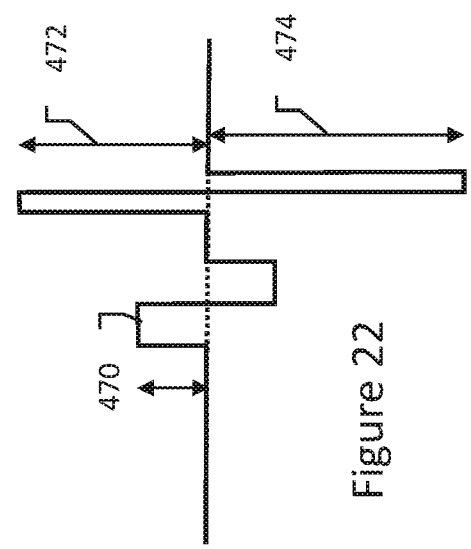

In still another example, which may use ranges as noted above generally with more particular relative ranges, a therapy pattern having two biphasic waveforms with more than two referenced amplitudes is shown in FIG. 22. Here, an initial biphasic waveform is shown at 470, which may have characteristics similar to that of waveform 460 in FIG. 21. A second biphasic waveform follows, with the second waveform being imbalanced. More particularly, an initial phase has a first amplitude 472, which is greater than the amplitude used in the first biphasic waveform 470, but less than the amplitude of the latter phase 474 of the second biphasic waveform. The recognition here is that the initial biphasic waveform 470 is likely to place more of the extracellular charged molecules on a first surface of the cells undergoing treatment than on any other surface, since the latter phase of the first biphasic waveform 470 occurs after some quantity of the charged molecules has already been removed from the extracellular fluid making for a lesser effective concentration. As a result, the first amplitude 472 is chosen for operation in conjunction with the applied substance to achieve irreversible electroporation on one cell surface, while the second amplitude 474 is chosen to achieve irreversible electroporation on a cell surface without the aid of the applied substance. In a further variant on the pattern of FIG. 22, the initial waveform 470 may be monophasic. In an example, the first amplitude 472 may be in the ranges noted above for waveforms 452 and 462, while the second amplitude 474 may be 20 percent to 100 percent larger than the first amplitude 472.

Figure 23:
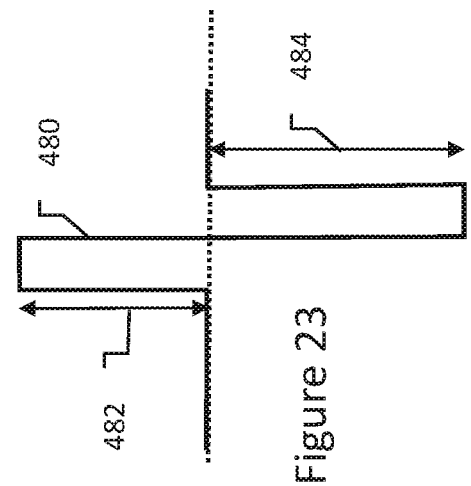

FIG. 23 shows another example. Here, a biphasic waveform is delivered at 480. A first phase has a first amplitude 482 which is less than the amplitude 484 of the second phase. The waveform shown may be delivered as a pre-pulse waveform to achieve desirable distribution extracellular molecules on the cell membrane, with the larger amplitude at 484 chosen to encourage a more equal distribution since the available concentration of charged molecules in the extracellular fluid will be lower than during the first phase of the biphasic waveform 480. The waveform may be delivered also as an electroporation inducing waveform, where the large amplitude at 484 is delivered for reasons similar to those given for waveform 474 in FIG. 22. In another example, the waveform of FIG. 23 is delivered as a pre-pulse waveform to achieve more uniform distribution of charged molecules on the cell membrane as described above, followed by a balanced biphasic waveform such as that at 452 in FIG. 20, adapted to induce irreversible electroporation.

Any of these waveforms as described relative to FIGS. 9 and 20-23 may be delivered in any of the systems herein.

Referring now to FIG. 14, again an organ 500 is shown with a target tissue 502 therein. A substance has been injected in, near or to all or a portion of the target tissue 502, as shown at 504. A first electrode 510 is shown on a catheter 512 that has been advanced using conventional methods through a body lumen 514 to a desired position near the target tissue 502. A second electrode 520 is shown on a catheter 522 that has been advanced using conventional methods through a body lumen 524 to a desired position near the target tissue 502. Biphasic therapy can then be delivered as shown at 530 between the electrodes 510, 520.

In FIG. 15, a target tissue 550 is shown. A substance has been injected in, near or to all or a portion of the target tissue 552, as shown at 554. A first electrode 560 and a second electrode 562 are shown on a catheter 564 disposed in a body lumen 566 near the target tissue 550. In this example, a biphasic waveform is applied as indicated at 570. The catheter 564 may be positioned and repositioned as needed to allow the generated field to capture different portions of the target tissue 552. If desired, an additional electrode may be placed remotely as well, and combination therapy may include biphasic waveforms between different pairs of electrodes including, for example, pairs of 560/562, 560/580, 562/580, as well as tripole configurations such as by linking electrodes 560/562 as a common pole relative to electrode 580 to allow the portions of the target tissue 550 farthest from the catheter 564 to be reached, or linking electrodes 560/580 as a common pole relative to electrode 562, which would allow steering of the current/field around the tumor.

In another example, more than two electrodes 560, 562 may be provided on the catheter 564. In yet another example, 2 or more electrodes may be placed on two or more catheters (such as in FIG. 14) on opposing sides of a target tissue with various pairings of electrodes used to spatially define the volume of interest to encompass as much of the target tissue as is desired.

FIGS. 16-17 show applying a substance to or near a target tissue using different systems. Referring first to FIG. 16, here a target tissue is shown at 600. A therapy catheter 610 extends through a body lumen 612 and has one or more electrodes 614 for later use in electroporation waveform delivery. The catheter 610 has a distal port 616 from which a needle 618 extends in a desirable direction. X-ray visualization, such as fluoroscopy, may be used to aid in directing the needle 618 toward the target tissue 600. Upon reaching the target tissue 600, and in some examples, piercing the target tissue 600, the needle 618 is used to inject a substance 620 such as a mixture of charged molecules, such as a cationic polymer, in a saline or other biocompatible liquid. The quantity injected may be determined based on an estimated volume of the target tissue. As noted previously, the needle may be advanced to a first position and a first quantity of material injected, and then moved to a different position and a second quantity of material injected, until a desired quantity and/or spatial distribution is achieved. Once the desired quantity of the substance is injected, the needle 618 is retracted into the catheter 610. Retraction via the catheter 610 likely reduces the occurrence of any track seeding, as the catheter itself 610 will be "cleaned" so to speak during therapy delivery using the electrodes. FIGS. 18-19 show an example design.

FIG. 17 shows another example. Here, a target tissue is shown at 650. A sheath 660 is advanced in a body lumen 662 to near the target tissue 650, and a microcatheter 670 is advanced therefrom to the target tissue 650. The substance is then injected as indicated at 680. Once the desired quantity is injected, the microcatheter can be withdrawn into the sheath and removed.

In any example herein where a body lumen is traversed by a catheter or sheath, conventional cannulation methods may be used including, for example, venous/arterial access methods (such as the Seldinger method), or biliary or other luminal access methods that traverse portions of the alimentary canal. A guidewire may be used in some examples to traverse complex anatomy and steer a path to a desired position. External imaging, such as X-ray or fluoroscopy, or other imaging systems, may be used. Ultrasound may also be used to track position of interventional instruments.

FIGS. 18-19 show a device useful for applying a substance in target tissue. Turning first to FIG. 18, a distal portion of a catheter is shown at 700, having a side port 702 with a ramp feature 704. A needle or microcatheter 710 is shown extending from the side port 702. The needle or microcatheter 710 may be steerable or may be adapted to curve in a predetermined manner on exiting the side port 702. A lumen (not shown) couples to an opening (not shown) at or near the tip of the needle or microcatheter 710 to allow injection of a liquid containing a desired substance useful to aid in electroporation.

FIG. 19 is a section view along line 19-19 of FIG. 18. Here it can be seen that the distal portion 700 of the catheter comprises the port 702 which is the terminus of a first lumen through the catheter, having a ramp at 704 that directs the needle or microcatheter (not shown) out through the port. A second port is shown at the distal tip at 706 and may be used to track over a guidewire during insertion of the catheter and/or for injection of other materials such as a contrast material useful for visualization.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of The claimed invention is:

1. A method of treating targeted tissue of a patient comprising:
    injecting a cationic polymer in the targeted tissue;
    placing at least first and second electrodes in a position relative to the targeted tissue;
    delivering a series of electrical pulses defining biphasic waveforms after injection of the cationic polymer using the first electrode and second electrode as follows:
    in a first phase of a biphasic waveform, using the first electrode as the anode, and the second electrode as the cathode to deliver a first pulse; and
    in a second phase of a biphasic waveform, using the first electrode as the cathode and the second electrode as the anode to deliver a second pulse.

2. The method of claim 1 wherein the step of delivering the series of electrical pulses is performed after the cationic polymer is injected and before the cationic polymer has had time to accumulate on cells of the targeted tissue, such that the first pulse causes a concentration of the cationic polymer on a first side of at least one cell of the targeted tissue, the first side being nearer the first electrode than the second electrode, and the second pulse causes a concentration of the cationic polymer on the second side of the at least one cell, the second side of the at least one cell being nearer the second electrode than the first electrode.

3. The method of claim 1 wherein:
    the series of pulses further includes at least a third pulse and a fourth pulse;
    the third pulse is delivered using the first electrode as the anode and the second electrode as the cathode, and an amplitude of the third pulse is larger than an amplitude of the first pulse; and
    the fourth pulse is delivered using the second electrode as the anode and the first electrode as the cathode, and an amplitude of the fourth pulse is larger than an amplitude of the second pulse.

4. The method of claim 3 wherein the first and second pulses are delivered to cause desirable spatial distribution of the cationic polymer, and the third and fourth pulses are delivered to cause irreversible electroporation of the at least one cell.

5. The method of claim 3 wherein the first pulse has a pulse duration that is greater than a pulse duration of the third pulse, and the second pulse has a pulse duration that is greater than a pulse duration of the fourth pulse.

6. The method of claim 3 wherein the third pulse and the fourth pulse each have pulse durations of less than 10 microseconds.

7. The method of claim 3 wherein the third pulse and the fourth pulse each have pulse durations of less than 1 microseconds.

8. The method of claim 1 wherein the step of injecting the cationic polymer is performed by inserting a syringe into the targeted tissue.

9. The method of claim 1 wherein the step of injecting the cationic polymer is performed by inserting a microcatheter into a vicinity of the targeted tissue.

10. The method of claim 1 wherein at least one of the first and second electrodes are disposed on a catheter that further comprises a lumen for delivering the cationic polymer, such that the step of injecting the cationic polymer is performed by injecting the cationic polymer via the lumen.

11. The method of claim 1 wherein an interpulse delay between the first pulse and the second pulse is less than about 2 microseconds.

12. The method of claim 1 wherein an interpulse delay between the first pulse and the second pulse is less than about 100 nanoseconds.

13. A method of treating targeted tissue of a patient comprising:
    injecting a cationic polymer in the targeted tissue;
    placing first and second electrodes in a position relative to the targeted tissue;
    delivering a series of electrical pulses after injection of the cationic polymer using the first electrode and second electrode as follows:
    in a first pulse, using the first electrode as the anode and the second electrode as the cathode and delivering the first pulse at a first amplitude for a first duration; and
    in a second pulse, using the first electrode as the anode and the second electrode as the cathode and delivering the second pulse at a second amplitude for a second duration;
    wherein the second amplitude is greater than the first amplitude and the second duration is shorter than the first duration.

14. The method of claim 13 wherein the first amplitude induces an electrical field in the targeted tissue of up to 650 volts per centimeter, and the second amplitude induces an electrical field in the targeted tissue in the range of about 750 to 5000 volts per centimeter.

15. The method of claim 13 wherein the first duration is in the range of about 10 to about 100 microseconds, and the second duration is in the range of about 1 to about 50 microseconds.

16. A method of treating targeted tissue of a patient comprising:
    injecting a cationic polymer in the targeted tissue;
    placing first and second electrodes in a position relative to the targeted tissue;
    delivering an electrical pulse to the targeted tissue after injection of the cationic polymer using the first electrode as anode and the second electrode as cathode by:
    in a first, initial portion of the electrical pulse, using a first amplitude for a first duration; and
    in a second, final portion of the electrical pulse, using a second amplitude for a second duration;
    wherein the second amplitude is greater than the first amplitude and the second duration is shorter than the first duration.

17. The method of claim 16 wherein the first amplitude induces an electrical field in the targeted tissue of up to 500 volts per centimeter, and the second amplitude induces an electrical field in the targeted tissue of over 500 volts per centimeter.

18. The method of claim 16 wherein the first duration is greater than 10 microseconds, and the second duration is less than 2 microseconds.

19. A method comprising:
a. performing a method as in claim 16;
b. waiting at least 5 minutes;
c. measuring an impedance within the targeted tissue to determine whether a desired amount of irreversible electroporation has taken place and, if not,
d. again performing steps a-c.

20. A method as in claim 16 wherein:
the cationic polymer is delivered in an amount insufficient to substantially destroy the targeted tissue without application of the series of electrical pulses; and
the series of electrical pulses are delivered at amplitudes and pulse durations that are insufficient to substantially destroy the targeted tissue without the cationic polymer.

* * * * *